US012279902B2

(12) United States Patent
Shechter et al.

(10) Patent No.: US 12,279,902 B2
(45) Date of Patent: Apr. 22, 2025

(54) SUPPRESSION OF MOTION ARTIFACTS IN COMPUTED TOMOGRAPHY IMAGING (71) Applicant: KONINKLIJKE PHILIPS N.V., Eindhoven (NL)

(72) Inventors: Gilad Shechter, Haifa (IL); Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 133 days.

(21) Appl. No.: 17/916,959

(22) PCT Filed: Apr. 6, 2021

(86) PCT No.: PCT/EP2021/058829
§ 371 (c)(1),
(2) Date: Oct. 4, 2022

(87) PCT Pub. No.: WO2021/204737
PCT Pub. Date: Oct. 14, 2021

(65) Prior Publication Data
US 2023/0148983 A1  May 18, 2023

(30) Foreign Application Priority Data

Apr. 8, 2020  (EP) .................................. 20168618.5

(51) Int. Cl.
*A61B 6/00*  (2024.01)
*A61B 6/03*  (2006.01)
(Continued)

(52) U.S. Cl.
CPC ............ *A61B 6/5264* (2013.01); *A61B 6/032* (2013.01); *G06T 5/70* (2024.01); *G06T 11/008* (2013.01); *G06T 2207/10081* (2013.01)

(58) Field of Classification Search
CPC ...... A61B 6/5264; A61B 6/032; A61B 6/4441; A61B 6/5258; A61B 6/563; G06T 5/70;
(Continued)

(56) References Cited

U.S. PATENT DOCUMENTS 10,282,820 B2    5/2019  Goshen
10,575,795 B2    3/2020  Zamyatin
(Continued)

FOREIGN PATENT DOCUMENTS

JP      2015089452 A    5/2015
WO   WO2019143333 A1   7/2019

OTHER PUBLICATIONS

PCT International Search Report, International application No. PCT/EP2021/058829, May 20, 2021.
(Continued)

*Primary Examiner* — Kiho Kim
(74) *Attorney, Agent, or Firm* — Larry Liberchuk (57) ABSTRACT

A system (SYS) and related method for motion artifact reduction in X-ray imaging. The system (SYS) comprises an input interface (IN) for receiving a first input image (i1, I1) of an object (PAT) reconstructed from a first set of projection data, and a second input image (i2, I2) of the object reconstructed from a second set of projection data. The second set is smaller than the first set. A motion analyzer (MA) establishes an estimate for motion corruption based on the two input images. A selective combiner (Σ) computes an image value for an enhanced image (I1+I2, i1+i2), based on the motion estimate and on image information in the first input image (i1, I1) and/or the second input image (i2, I2).

8 Claims, 3 Drawing Sheets

(51) Int. Cl.
*G06T 5/70* (2024.01)
*G06T 11/00* (2006.01)

(58) Field of Classification Search
CPC ......... G06T 11/008; G06T 2207/10081; G06T 2211/412; G06T 11/006
See application file for complete search history.

(56) References Cited

U.S. PATENT DOCUMENTS

| | | |
|---|---|---|
| 10,702,234 B2 | 7/2020 | Jain |
| 2004/0076265 A1 | 4/2004 | Heuscher |
| 2004/0125908 A1 | 7/2004 | Cesmeli |
| 2008/0051648 A1* | 2/2008 | Suri ................... A61B 6/5264 600/407 |
| 2011/0142315 A1 | 6/2011 | Hsieh |
| 2012/0294414 A1 | 11/2012 | Koehler |
| 2013/0202166 A1 | 8/2013 | Koehler |

OTHER PUBLICATIONS

Barrett J.F. et al., "Artifacts in CT: Recognition and Avoidance", Radiographics, vol. 24, No. 6, pp. 1679-1691, 2004.

Heuscher D. et al., "Redundant Data and Exact Helical Cone-Beam Reconstruction", Physics in Medicine & Biology, vol. 49, pp. 2219-2238, 2004.

Grass M. et al., "Motion Compensation for Non-Gated Helical CT: Application to Lung Imaging", SPIE Proceedings, vol. 10573, Medical Imaging 2018: Physics of Medical Imaging; 105733H. Jun. 2018.

Scechter G. et al., "The Frequency Split Method for Helical Cone Beam Reconstruction", Medical Physics, vol. 31 Issue 8, pp. 2230-2236, 2004.

\* cited by examiner

SUPPRESSION OF MOTION ARTIFACTS IN COMPUTED TOMOGRAPHY IMAGING

FIELD OF THE INVENTION

The invention relates to systems for motion artifact reduction in X-ray imaging, to a method for motion artifact reduction in X-ray imaging, to an imaging arrangement, to a computer program element and to a computer readable medium.

BACKGROUND OF THE INVENTION

Computed tomography (CT) imaging of the thorax is one of the most frequent applications of CT in radiology. A significant number of examinations suffer from motion artifacts, due, for example, the inability of patients to hold their breath or due to hiccups or coughing. Because of motion artifact, images may become non-diagnostic or at least are degraded in image quality. Image retakes may be required which incur additional costs in terms of time, computational resources and dosage sustained by patient and/or personnel.

In order to correct for motion artifacts, motion compensated reconstruction algorithms were proposed. Example is the approach discusses by M Grass et al in "Motion compensation for non-gated helical CT: application to lung imaging", published in Proc. SPIE 10573, Medical Imaging 2018, Physics of Medical Imaging, 105733H (9 Mar. 2018).

However, computational overhead in some motion compensated reconstruction schemes may be considerable.

SUMMARY OF THE INVENTION

There may therefore be a need for improved X-ray imaging. In particular, there may be a need for a computationally cheaper way to reduce motion artifacts.

The object of the present invention is solved by the subject matter of the independent claims where further embodiments are incorporated in the dependent claims. It should be noted that the following described aspect of the invention equally applies to the method for motion artifact reduction in X-ray imaging, the imaging arrangement, to the computer program element and to the computer readable medium.

According to a first aspect of the invention there is provided a system for motion artifact reduction in X-ray imaging, comprising:
  one or more input interfaces for receiving a first input image of an object reconstructed from a first set of projection data, and a second input image of the object reconstructed from a second set of projection data, the second set being smaller than the first set, and/or the second data set includes less redundant data than does the first set;
  a motion analyzer configured to establish an estimate for motion corruption based on the two input images; and
  a selective combiner configured to compute an image value for an enhanced image, based on the motion estimate and on image information in the first input image and/or the second input image.

Preferably, operation of the motion analyzer is based on forming a difference image between the two input images, and analyzing the difference values making the difference image. The larger an (absolute) difference value, the more motion corruption there is at a given image location.

The combiner operates in a selective manner by combining the enhanced image from image information from either one of the two input images at certain image locations or by combining or "mixing" image information from both input images at certain other image locations, each depending on the respective motion estimate per image location.

In embodiments, the selective combiner is configured to combine the image information from either one or both of the input images so that a relative contribution of image information from the two input image varies with the motion estimate.

In embodiments, the selective combiner is configured to combine the image information from either one or both of the input images so that a contribution of image information from the first or second input image varies with the motion estimate, at the expense of a contribution of image information from the second and first input image, respectively.

In embodiments, a contribution of information from the second image is the higher, the higher the level of motion corruption indicative by the motion estimate, and wherein the contribution of information from the first image is the higher, the lower the level of motion corruption indicative by the motion estimate.

More specifically, in embodiments, the relative contribution is determined by a hard or a soft thresholding scheme. In a hard thresholding, the motion analyzer furnishes a binary analysis on whether or not there is motion corruption at a given image location. If there is, the corresponding image value from the second image is taken as the image value of the enhanced image. If there is no motion (or the motion is below a "hard" threshold), the corresponding image value from the first image is taken as the image value of the enhanced image at the said image location. In a soft thresholding, the image values of the enhanced image are mixed for a given image location from image values from both input images, in proportion based on the amount of motion as established by the estimate.

In embodiments, the system comprises a de-noiser applied to initial input images to obtain the two input images as received at the one or more input interfaces. In other words, the input images are de-noised first and it is the so de-noised images that are then analyzed by the motion analyzer to establish the estimate. De-noising first, allows for more robust motion estimates.

In embodiments, the projection data acquired by computed tomography imaging apparatus.

In another aspect there is provided a method for motion artifact reduction in X-ray imaging, comprising the steps of:
  receiving a first input image of an object reconstructed from a first set of projection data, and a second input image of the object reconstructed from a second set of projection data, the second set being smaller than the first set;
  establishing an estimate for motion corruption based on the two input images; and
  computing an image value for an enhanced image, based on the motion estimate and on image information in the first input image and/or the second input image.

In embodiments, the method comprises the step of first denoising one or both of the two input images and to then establish the estimate based on the two (now denoised) input images.

In another aspect there is provided an image arrangement, comprising:
  the system of any one of previously mentioned embodiments; and
  the imaging apparatus.

In another aspect there is provided a computer program element, which, when being executed by at least one processing unit, is adapted to cause the processing unit to perform the method as per any one of the above mentioned embodiments.

In another aspect still, there is provided a computer readable medium having stored thereon the program element.

In embodiments, the second set of projection data may be a subset of the first set. The first set may comprise all available projection data collected in a scan operation by a tomographic or tomosynthetic imaging apparatus, whilst the second set is a part thereof. However, it is not necessary herein in all embodiments for the first set to include all the collected projection data. Some projection data are collected to include redundancies, such as in cone beam CT or other (divergent) scan geometries or techniques. The first set is envisaged to include more (or in some embodiments all) redundant data than does the second set. In embodiments the second set does not include redundancies.

What is proposed herein is a novel approach to reduce or suppress motion artifacts. Motion can be reduced without performing a computationally expensive motion compensated reconstruction. Instead, in proposed system first reconstructs an original image using some or all available redundant data from collected projection data. To suppress or at least reduce cone beam artifacts (CBA) in this image, one may use a frequency split (FS) reconstruction method, to be described more fully below. In addition, the second image is reconstructed using a smaller amount of the available redundant projection data compared to the projection data used for the reconstruction of the original image. The motion artifacts in this second image are generally (much) smaller than in the original image. De-noising these two images and comparing same helps detect image locations where the original (the first) image suffers from motion artifacts caused by motion, eg of the patient or untended motion of the imaging equipment. The enhanced image is hybrid combined from both input images. The enhanced image is more similar to the second image in motion corrupted image locations (eg, regions), but is more similar to the original image in all other image locations.

The proposed method and system is faster, simpler to implement and more robust since it obviates the need for any complex computational steps as otherwise required in motion compensated reconstruction ("MCR") algorithms. In particular, the proposed method and system do not require (elastic) image registration and/or estimation of a motion field. The proposed method is robust since in regions where no, or only little, motion is detected, the enhanced image equals (or at least resembles) the original nominal image and is hence left unchanged.

While in MCR CBA can distort the required estimation of a motion field, in the proposed method and system, the detection by the motion analyzer of motion artifact corrupted regions is largely insensitive to CBA, in particular (but not only) when the FS reconstruction is used.

The proposed system improves image quality of lung and thorax images that otherwise may suffer from breathing or heart motion artifacts.

Definitions

"user" relates to a person, such as medical personnel or other, operating the imaging apparatus or overseeing the imaging procedure. In other words, the user is in general not the patient.

"object" is used herein in the general sense to include animate "objects" such as a human or animal patient, or anatomic parts thereof but also includes inanimate objects such as an item of baggage in security checks or a product in non-destructive testing. However, the proposed system will be discussed herein with main reference to the medical field, so we will be referring to the "object" as "the patient" and the location or region of interest ("ROI"), being a particular anatomy or group of anatomies of the patient.

The terminology "first" and "second" (image, subset, etc) is purely for naming and distinction purposes and does not imply temporality or hierarchic relationships.

"Image location" as used herein may indicate a single pixel/voxel position, or may indicate location of a larger image portion or image region, comprising plural pixels/voxels such as a patches, neighborhoods of any shape and size, tiling the respective image.

BRIEF DESCRIPTION OF THE DRAWINGS

Exemplary embodiments of the invention will now be described with reference to the following drawings, which, unless stated otherwise, are not to scale, wherein.

DETAILED DESCRIPTION OF EMBODIMENTS

Figure 1:
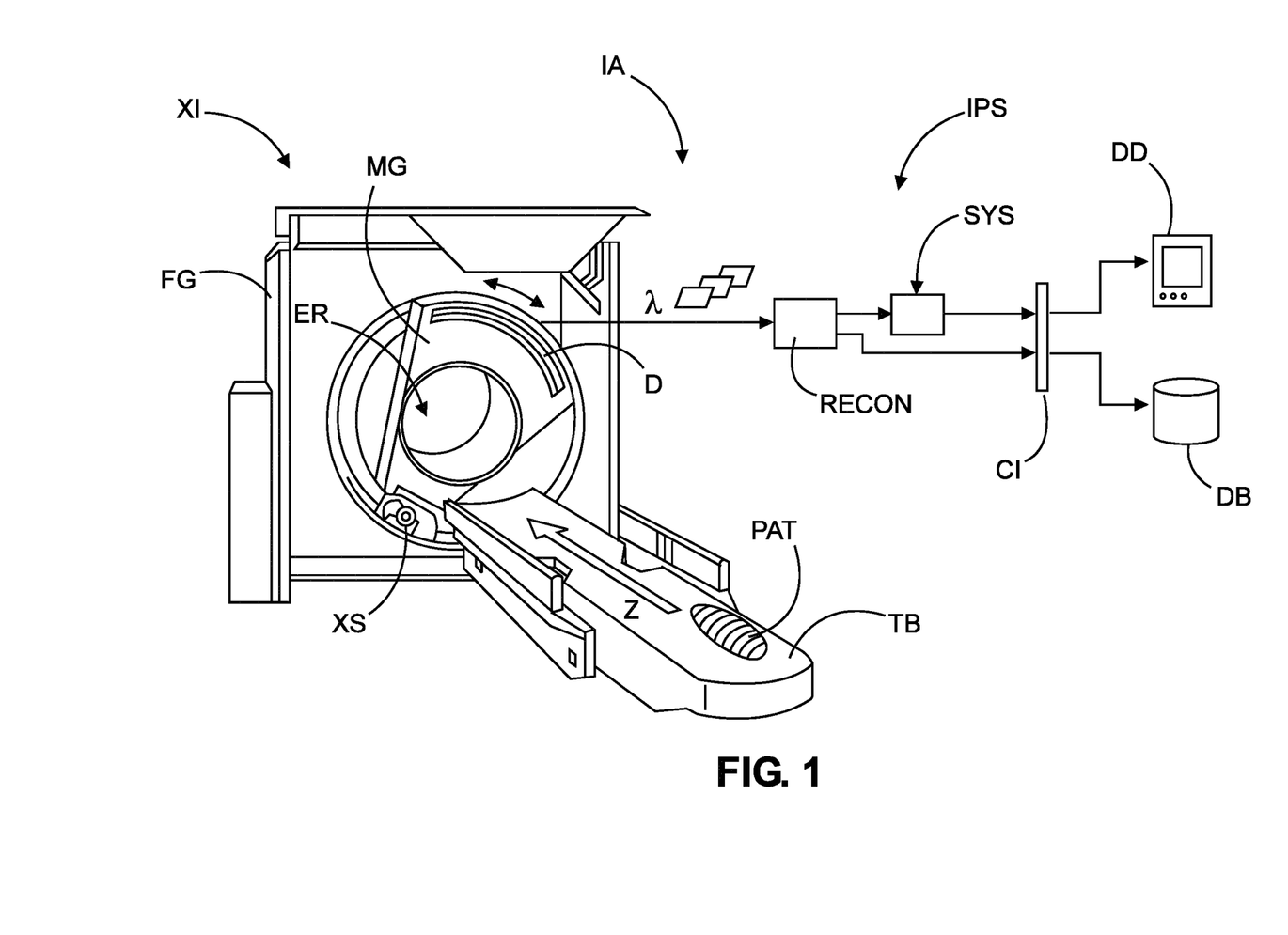
FIG. 1 shows a schematic block diagram of an imaging arrangement.

With reference to FIG. 1 there is shown an imaging arrangement IA envisaged herein in embodiments.

The imaging arrangement IA includes an X-ray imaging apparatus XI that is configured to acquire images of an object PAT such as a human or animal patient.

The images acquired by the imaging apparatus, or imagery derivable therefrom, may be processed by a computerized image processing system IPS to produce enhanced imagery as explained in more detail below.

The enhanced imagery may be passed through a communication interface CI to be stored in memory DB, such as in a data base system, or may be visualized by a visualizer VIS on a display device DD, or may be otherwise processed.

The imaging apparatus XI ("imager") envisaged herein is in particular of the tomographic type.

In this type of imaging, also referred to a rotational imaging, projection images λ are acquired by the imager of a ROI of patient PAT. The projection images may then be re-constructed by a re-constructor RECON into axial or cross-sectional images or "slices". The axial imagery may reveal information about internal structures of the ROI to inform examination and diagnosis by clinicians in line with clinical goals or objectives to be achieved. Particularly envisaged herein are X-ray based imagers, such as computed tomography (CT) scanners, or C-arm/U-arm imagers, mobile, or fixedly mounted in an operating theatre, etc.

The imager XI includes an X-ray source XS and an X-ray sensitive detector D. The imager XI may be configured for energy integrating imaging or for spectral imaging (also referred to as energy discriminating imaging). Accordingly, the detector D may be of the energy integrating-type, or of the energy discriminating type, such as a photon-counting detector. Spectral (volumetric) image data may include for example, low energy high contrast image, an effective Z (atomic number) image, a virtual monochromatic image, a contrast agent quantitative map, a virtual non-contrast image, an electron density image, and/or other type of spectral imagery. For spectral imaging, the imager XI may include components to acquire multi-energy projection data. The said components may include a dual X-ray sources XS,XS' (not shown), and the detector D may be arranged as a dual layer detector, or as the said photon-counting detector. Spectral image processing components of the image processing system IPS convert may process the multi-energy projection data into the spectral imagery.

During image acquisition, patient PAT resides in an examination region ER between the source XS and detector D. In embodiments, the source X-ray moves in an imaging orbit or scan path in a rotation plane around an imaging axis Z. Helical scan paths are also envisaged. The rotation may be achieved by having imager XI include a stationary gantry FG and a rotating gantry MG. The rotating gantry MG is rotatably supported by the stationary gantry FG. The rotating gantry RG rotates around the examination region ER and at least a portion of subject PAT therein, and about the imaging axis Z. The radiation source XS, such as an x-ray tube, is supported by and rotates with the rotating gantry MG around the examination region ER. The imaging axis passes through the ROI. Preferably, the patient's longitudinal axis is aligned with the imaging axis Z, but other arrangements and geometries are also envisaged.

Imaging geometries envisaged herein include parallel beam CT geometry, and, preferably, divergent beam geometry (i.e., fan or cone beam geometry). An imaging orbit with a rotation of the source XS around the ROI in an arc of at least 180° constitutes a full scan. However, sometimes only a limited angle scan is performed due to time or space constraints or other. In such as limited angle scan, the scan path subtends a rotation angle of less than 180°.

During the rotation, the source XS emanates an X-ray beam XB and irradiates the ROI. During the rotation, the projection images are acquired at the detector D from different directions q. The X-ray beam XB passes along the different directions through the patient PAT, particularly through the ROI. The X-ray beam interacts with matter in the region of interest. The interaction causes the beam XB to be modified. Modified radiation emerges at the far end of the patient and then impinges on the X-ray sensitive detector D. Circuitry in the detector converts the modified and impinging radiation into electrical signals. The electrical signals may then be amplified or otherwise conditioned and are then digitized to obtain the (digital) projection imagery $\lambda$ which may then be reconstructed into the axial sectional imagery by a reconstructor RECON.

The re-constructor RECON is a computer implemented module that runs a reconstruction algorithm, such as FBP (filtered back-projection), Fourier-domain based reconstruction algorithms, algebraic (ART) reconstruction algorithm, or iterative reconstruction algorithms. More recent machine learning ("ML")-based reconstruction algorithms, such as artificial neural networks (in particular convolutional neural networks) suitably trained, are also envisaged.

In embodiments, a cone beam reconstruction algorithm is used. In embodiments, the reconstruction algorithm is adapted for helical scan paths.

The re-constructor RECON module may be arranged in hardware or software or both. The re-constructor RECON transforms the projection images $\lambda$ acquired in the projection domain of the detector D into the axial sectional imagery in image domain. Image domain includes the portion of space in the examination region where the patient resides during imaging. In contrast, the projection domain is located in a X-ray radiation sensitive surface or layer of the X-ray detector D. In the image domain, the re-constructed imagery is defined in cross sectional planes parallel to the rotation plane(s) of the orbit and perpendicular to the imaging axis Z. Different axial images in different cross sectional planes can be acquired, that together form a 3D image volume, a 3D image representation of the ROI. The 3D volume may be acquired by advancing the support table TB on which patient PAT resides during imaging, such as in a helical scan path. Alternatively, or in addition, it is the stationary gantry FG that is translated. The relative translational motion of patient PAT versus source XS along axis Z and the rotation of source XS around axis Z give rise to the helical scan path at a certain pitch. The pitch may be fixed or is user adjustable. In non-helical scans, the scan path in general subtends an arc of up to, or substantially equal to, 180° (plus fan angle).

The projection data $\lambda$ as acquired in the scan comprises a number of different projection images, or "frames. In particular, to each position $q_i$ of the source XS on the scan path corresponds an associated projection frame associated with that position.

In certain imaging geometries, such as helical geometries, the projection data $\lambda$ acquired includes redundancies due to the pitch, the width of the beam cone (measured by the cone angle), and the width of the detector surface. This is because some detector pixels will register the same intensity in different projection frames as exposure occurs along the same geometrical ray through the imaged object OB from different scan orbit positions $q_i$, $q_j$.

When patient motion occurs during acquisition of the projection data $\lambda$, motion artifacts are incurred in the reconstructed imagery. The patient motion may be voluntary but may most often be involuntary such as motion caused by coughing or by cardiac and/or respiratory activity. Motion artifacts are image structures that do not represent actual tissue or anatomies. In extreme cases, heavy motion artifacts can render a reconstructed image useless thus incurring unnecessary time for retakes and computational resources for additional reconstructions.

To combat motion artifacts in reconstructed imagery, the proposed image processing system IPS includes a motion artifact reduction or suppressor system SYS. Broadly, the motion artifact reducer SYS converts a possibly motion artifact corrupted input image I into an enhanced image I' having fewer or no such motion related artifacts.

The proposed motion artifact reduction system SYS (also referred to herein briefly as "motion reducer") implements a two channel approach where two versions i1, i2 of reconstructed images are received as input and processed into the enhanced image I'.

The two input images i1, i2 are reconstructed from different sub-sets $\lambda 1$, $\lambda 2$ of the original projection data $\lambda$. In particular, the first image i1 (also referred to herein as the "fat image") is reconstructed from a larger set of projection data $\lambda 1$ than is the second image I2 (referred to herein as the "lean image"), which is reconstructed from a smaller subset $\lambda 2 \subset \lambda$. More particularly, and as will be explored more dully below, the projection data set $\lambda 1$ from which the fat image i1 is reconstructed includes more redundant data than does the smaller subset $\lambda 2$ from which the lean image i2 is reconstructed. In one embodiment mainly envisaged herein (but not necessarily in all embodiments), the fat image i1 is reconstructed from all projection data $\lambda 1 = \lambda$, whereas the lean image i2 is reconstructed from a sub-set $\lambda 2$ of the original projection data $\lambda 1 = \lambda$. If even $\lambda 1$ does not comprise all data $\lambda$, $\lambda 2$ may still be a subset of $\lambda 1$.

Broadly, the motion reduction system SYS operates to form the enhanced image I' as a hybrid image derived from the two input images i1, i2. Image information from the two input images I1, I2 is selectively combined into the hybrid image I'.

More specifically, two reconstructions are performed based on the two different sub sets $\lambda 1$, $\lambda 2$ of the original projection data $\lambda$ acquired during the scan. Yet more particularly, in addition to a "nominal" reconstruction, the fat image i1, we reconstruct herein a second image, the lean image i2, but this time using only a (small) part of available redundant data. By comparing these two images i1,i2 (preferably after de-noising), we may detect image locations in the original fat image i1 that suffer from patient motion/motion artifact corruption. Patient motion can be more readily distinguished with respect to the residual noise left after image de-noising. At these locations we replace the original image values in i1 by image values of the second image i2 in the detected image locations, to so assemble the enhanced image. In some or all other regions we avoid this replacement, thus keeping the low level of residual noise. Alternatively, a softer thresholding or replacement scheme is used where the image value for the enhanced image is computed as a weighted sum from both images i1,i2, with proportional contribution from each i1, i2, and as a function of the amount of motion detected.

In particular, in combining image information selectively from the two input images i1,i2, the proposed motion reduction system SYS uses an opportune selection policy to negotiate the following two opposing effects: because the fat image i1 is reconstructed from the larger projection data set $\lambda 1$ including more redundancies, i1 is more prone to motion artifacts but, at the same time, includes less noise, whereas the lean image i2 is reconstructed from the smaller projection data set with fewer redundancies and is more robust against motion artifacts but, as a down side, includes more image noise.

The proposed motion reduction system SYS judiciously combines information from both input images to reduce motion artifacts in the enhanced image, but at the same time does not incur more noise. According to one selection policy, for image locations that are more corrupted by motion image, more information from the lean image i2 is used, whereas for image locations with less motion corruption, more image information from the fat image i1 is used, at the expense of i2.

Figure 2:
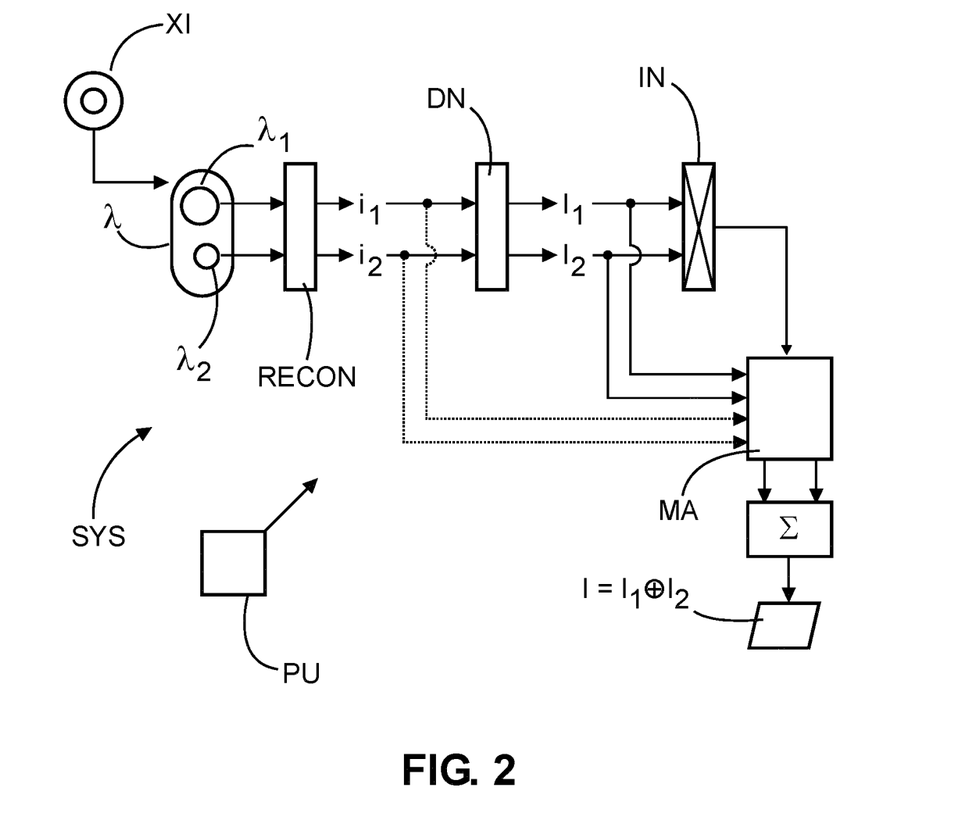
FIG. 2 shows a block diagram of an image processing system for reducing motion artifacts in imagery.

Reference is now made to the block diagram of FIG. 2 to explain operation of the motion reduction system SYS in more detail. The two input images, the fat and lean images i1, i2, reconstructed from respective different projection data sub-sets $\lambda 1$, $\lambda 2$ are received at one or more input ports IN.

A motion analyzer MA analyzes the two images input images i1, i2 to establish for each image location (pixel, voxel or a neighborhood/patch) whether there is or is no (or negligible) motion corruption. That, the analysis produces a binary motion map. In other embodiments, but not all, the motion analyzer MA quantifies the amount of motion corruption at some or each location j. In other words, motion analyzer MA outputs a motion corruption map that quantifies for each image location the amount of motion corruption.

Based on this motion map (binary or quantified), a selective combiner $\Sigma$ then selectively combines image information from the two input images i1, i2 to form the enhanced image I', now including fewer motion corruption artifacts than the input images. Preferably, there are no motion artifacts at all in the enhanced image.

Optionally and preferably, there is a de-noiser DN that first applies a de-noising algorithm to the respective fat and lean reconstructions i1 and i2 reconstructed respectively from the two projection data sets $\lambda 1$, $\lambda 2$ to obtain de-noised fat and lean reconstructions I1, I2 that are then analyzed by the motion analyzer MA. Such de-noising is preferable because it allows reducing the noise level so that the motion analyzer MA can more robustly quantify and distinguish contributions from motion. In the following reference is mainly made to the two de-noised versions I1,I2 when explaining operation of motion reducer MA and related method (at FIG. 3). However, the de-noiser DN, preferable as it is, is optional and all that is explained and stated below in respect of I1,I2, is understood to equally apply to i1,i2.

The combination operation by the selective combiner $\Sigma$ can be based on a hard or soft thresholding selection policy. In hard thresholding, the motion map is essentially a binary map indicating for each image location whether or not there is motion corruption, based on a threshold. This can be done by assigning for instance, the value "1" to the case where there is no motion corruption and encoding "0" when there is motion corruption. Other encodings are also envisaged. In this simple hard thresholding scheme, at a certain image location where there is motion corruption, the respective image value at the given image location is copied from the second image I2. But if there is no motion corruption at a given image location as per the map, an image value for that image location is copied from the original reconstruction I1.

Preferably, instead of such a hard thresholding, a soft thresholding is used where image values of the enhanced image I' are mixed from the two input images I1,I2, in dependence on the amount of motion artifact corruption, with image information drawn from the fat I1 image given more weight the less motion there is at an image location, and with less weight given to image information drawn from the lean image, and vice versa if the amount of motion ascertained by motion analyzer MA is higher.

In embodiments this mixing is accomplished by computing the enhanced image I' as a weighted sum of the input images I'=$\alpha$I1+$\beta$I2, where weights $\alpha$, $\beta$ in general vary with the motion corruption per image location j. The weights are positive numbers. In particular, a given image value $y_j \in$ I' at image location j is computed as a weighted sum
$\alpha_j x_1^j + \beta_j x_2^j$, with weights $\alpha_j$, $\beta_j$ for image location j, and the x's indicating respective image values drawn from the two input images I1,I2 at location j. In this embodiments, the motion map comprises the weights $\alpha_j$, $\beta_j$ which may be conceptualized as a weight image $I_w$. The weights $\alpha$, $\beta$ (to ease notation, we may drop the location index j on occasion) can be normalized, or instance are configured to add up to a constant value such as unity "1". The weights $\alpha,\beta$ measure the preponderance of motion corruption at the given image location. In particular, the weights measure the amount of motion detected by motion analyzer MA. The more motion there is, the higher the contribution at the given image location drawn from the second image I2 and, conversely, the lower the contribution from the original image I1 and vice versa for the case where there is little image corruption at a given image location. In yet other words, a given contribution from one of the two images I1,I2 at a given location is at the expense of the contribution from the other image I2,I1, and this adverse relationship is reflected in the weights: the higher one of the weights, the lower the other. The functional relationship between the weights $\alpha$, $\beta$ and the registered amount of motion may be a linear, or may be based on any other monotone function, such as a soft-max function, or a section of a sinusoidal function, or other.

Specific examples of such a motion versus weight relationship for the purposes of computing the hybrid image are discussed further below at FIG. 3 to which reference is now made.

Figure 3:
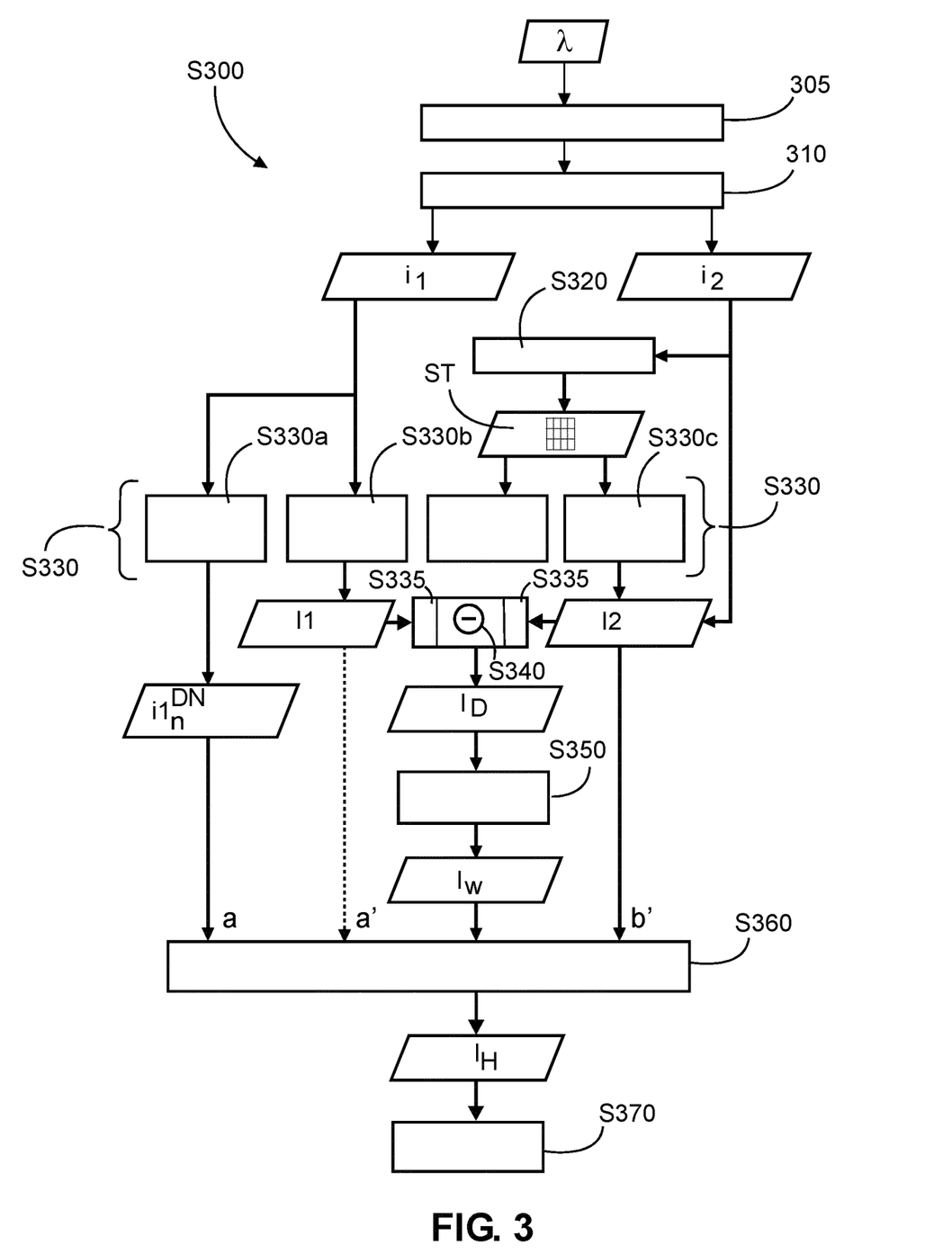
FIG. 3 is a flow chart of an image processing method for reducing motion artifacts.

Specifically, FIG. 3 is a flow chart of an image based method for motion artifact reduction. Whilst the method steps discussed in more detail below may be understood as one way to implement the above mentioned system for motion reduction system SYS, it will also be appreciated that the method is not necessarily tied to the architecture of the system in FIGS. 1,2 discussed above. In particular, the following steps may be understood as a teaching in their own right, not necessarily tied to the architecture in FIGS. 1,2.

At step S305, sets of projection data $\lambda \supseteq \lambda 1$, $\lambda \supset \lambda 2$ are received, as acquired in a rotational X-ray imaging apparatus at a given imaging geometry such as cone beam, fan beam, parallel beam or other.

At step S310, two input images, the fat and lean image, i1, i2 are reconstructed from the respective projection datal $\lambda 1$, $\lambda 2$ as received at step S305. Preferably, fat image i1 is reconstructed from all available projection data including in particular all available redundant data. The lean image i2 is reconstructed from a sub-set $\lambda 2 \subset \lambda$ of all available projection data $\lambda$. The smaller set $\lambda 2$ includes in particular less redundant data than $\lambda 1$ does. It will be understood however that it is not necessary to reconstruct i1 from all available (redundant) projection data $\lambda$. It may suffice for $\lambda 1$ to be a true sub-set $\lambda 1 \subset \lambda$, as long as the sub-set $\lambda 1$ includes more redundant data than the smaller sub-set $\lambda 2$ does.

Especially for cone beam reconstructions mostly envisaged herein, at step S310, special reconstruction algorithms may be used to reduce cone beam type artifacts ("CBA"). One such class of reconstruction algorithms with CBA artifact reduction include frequency spilt ("FS")-type reconstruction methods ("FSR"). See for instance G Schechter et al in "*The frequency split method for helical cone-beam reconstruction*", published in Med. Phys. 31 (8), August 2004, pp 2230-2236. In FS-type reconstructions, image information in two spatial frequencies bands, high and low, are reconstructed separately into two images by filtered back projection. In each case, a different filter is used. The two images, the high frequency range image and the low frequency range image, so obtained are then added up. The FS approach helps reduce CBA. FS reconstruction algorithm types, or related reconstruction algorithms, are envisaged herein for the reconstruction of the fat image i1. As mentioned, preferably all available redundant data $\lambda 1$ is used for the reconstruction of i1, or at least more redundant data is used than for the reconstruction of lean image i2. Reducing CBA helps avoid false positive detection in motion analysis at step S340 (to be discussed more fully below).

The lean image i2 may be reconstructed from a subset of projection data $\lambda 2 \subset \lambda$, in particular $\lambda 2 \subset \lambda 1$, with less or no redundancy. In the context of the FSR, this smaller subset $\lambda 2$ may be selected as frames that are associated with the angular sub-range of parallel projections used to reconstruct the low-frequency range image. For a typical scan pitch value of around 1 or below, this range of parallel projections $\lambda 2$ contains no or only a small part of redundant data. Therefore, the motion artifacts are less pronounced in the lean inmage i2 than they are in the fat image i1. However, the reconstruction of the two images i1,i2 is not confined to FSRs, and other reconstructions schemes, preferably with low CBA, are also envisaged. The selection of the subset $\lambda 2$ may be done by other schemes than parallel projection rebinning as in FSR based embodiments. The selection may be done by random, or by choosing every k-th frame from $\lambda$, with step k large enough to avoid overlaps, etc.

At an optional step S330 the two reconstructed input images i1, i2 are de-noised by a de-noising algorithm to reduce the noise level and derive de-noised versions of i1,i1, namely fat image $I_1^{de-noised}$ and lean image $I_2^{de-noised}$. Different embodiments for the de-noising step S330 are envisaged.

In one embodiment, the de-noising is structure based. In more detail, an image structure calculation S320 is performed to isolate image structures such as transitions, borders etc. The result of the structure calculation at step S320 is a volumetric structure ST. The structure calculation S320 may be based on a segmentation. Preferably, the structure ST is computed in the lean image i2. The structure ST is expected to be more clearly defined as compared to computing the structure ST in the fat image i1, although computing structure ST from i1 may still be done in alternative embodiments.

In structure based de-noising, the noise contribution is calculated based on the image structure ST computed in step S320, such as edges, borders etc. Image contributions that are recognized to stem from noise are then subtracted or otherwise removed from the input imagery i1, i2 to arrive at the de-noised versions $I1=i_1^{de-noised}$ and $I2=i_2^{de-noised}$. In one embodiment, the structure-based de-noising is performed at step S330c on lean image i2, based on the volumetric structure ST computed in the lean image i2 itself, to arrive at the lean de-noised version I2 of lean image i2.

Alternatively, or in addition, at step S330B a structure propagation based de-noising is performed on the fat image i1 based on structure ST stemming from lean image i2. In other words, at step S330b structure propagation based de-noising is performed. Fat image i1 is de-noised based on image information ST propagated from the other image, the lean image i2. Structure propagation based de-noising is described in Applicant's U.S. Pat. No. 10,282,820.

As a variant of this structure propagation, at step S330a a "nominal" de-noising is performed that is natively based on structure in i1 itself, without recourse to additional information from image i2. In embodiments, the nominal image may be computed by iterative model based (IMR) reconstruction. Step S330A results in a nominal de-noised image $i1_{nominal}^{de-noised}$ (denoted as $i1_n^{DN}$ in FIG. 3).

The nominal de-noising of fat image i1 and/or the de-noising of lean or fat image is not necessarily structure based, and any other suitable de-noising algorithms are also envisaged. The structure calculation step S320 is hence optional.

The (original) fat image i1 and the lean images i2, or the de-noised fat and lean images I1,I2 are then received at step S335 and used at step S340 to establish the amount of motion corruption. This can be done in one embodiment by forming the image location-wise, such as pixel-wise, difference image $I_D$ by subtracting i1,i2 or I1,I2. The order of the subtraction is immaterial. In the following, pixel-wise processing will be assumed, without loss of generality, as more coarse-grained processing in terms of patches and neighborhood, possibly with suitable averaging as also envisaged in embodiments. The pixelwise absolute differences $|x_1^j - x_2^j|$ correlate with motion. The larger the difference, the larger the amount of motion. The pixelwise difference is hence a measure of motion. A binary thresholding may be done based on the pixelwise difference to decide whether or not there is motion at each location. A binary map may be provided, indicating per image location, where or not there is motion.

In embodiments, the differences $|x_1^j - x_2^j|$ may be mapped by a measure function $F^M$ to another measure to quantify the motion amount. This motion measure may then be used for a soft-thresholding rather than a hard, binary thresholding.

In an embodiment of soft-thresholding, weights $w = \alpha, \beta$ are computed per image location in an optional step S350 based on the difference image $I_D$. The weights may be organized in a motion map or weight image $I_w$. As the weights $w_i$ are computed per image location (pixel, voxel, patch/neighborhood), they can be organized into a weight image $I_w$ or non-binary motion map.

The weights determine the preponderance of image information from the two images to be taken, as function of the measured motion amount. There are hence two weights $w_i = (\alpha_i, \beta_i)$ for each image location $x_i$, one for I1, and one for I2. The map $I_w$ controls in what proportion image information is drawn from the fat and lean imagery I1, I2 to build up the enhanced image $I' = I_H$.

At step S360 the selective combination is then performed based on the weights $I_w$ to arrive at the hybrid image $I' = I_H$. In embodiments, the enhanced image $I'$ is a linear combination of the fat and lean imagery. Specifically, $I'$ is as a pixel-dependent weighted sum of two images. In more detail, different embodiments for the combination step S360 are envisaged.

In one embodiment, and is shown by arrows "a", "b" in FIG. 3, the enhanced image $I'$ is formed as a linear combination of de-noised lean image $I_2^{de-noised}$ and the nominal fat image $i1_{nominal}^{de-noised}$, with the weights $w(i)$ at location i as per $I_w$:

$$I_{hybrid}(i) = w(i) \cdot i1_{nominal}^{de-noised}(i) + (1 - w(i)) \cdot I2(i) \quad (1)$$

In an alternative embodiment, and as indicated by arrow combination "b", "a" in FIG. 3, $I2 = i_2^{de-noised}$ image is linearly combined with $I1 = i_1^{de-noised}$, based on weights as per $I_w$, with index i indication image location:

$$I_{hybrid}(i) = w(i) \cdot I1(i) + (1 - w(i)) \cdot I2(i) \quad (2)$$

At step S370 the enhanced image $I_H$ is output. Enhanced image $I_H$ may be displayed, stored in memory or may otherwise be processed or transmitted as required.

Referring now to weight generation step S350 in more detail, this may be based on the motion measure provided by the motion analysis step S340. The motion or motion artifact analyzer step is a mapping $F^M$: I1, I2 $\rightarrow$m, with m a positive number that varies with the amount of motion. As mentioned, in some embodiments $m = F^M = |I1 - I2| = I_D$ (or $I_D = |i1 - i2|$ in case no de-noising is done) is the absolute pixelwise difference of the fat and lean images, or a function thereof $f(|I1 - I2|)$, such as the squared difference $F^M = (I1 - I2)^t$, $t = 2$ or for other powers $t > 2$. The $\ell_p$ norm or $p^{th}$-powers thereof may be used.

The weight generation step S340 step maps the motion measure m to a set of weights based on a function $I_w$: $m \rightarrow \alpha, \beta \in [a, b]$. The weights are preferably normalized so ad up to a constant number such as unity. Without loss of generality, the weight interval $[a, b]$ may be taken as the unit interval $[0, 1]$. The weights $\alpha, \beta \in [0, 1]$ measure the proportion of contributions from the two input images I1, I2 as a function of motion m, for a given image location j in $I'$.

The function $I_w$ is preferably monotone over $[0, 1]$. The function $I_w$ may be based on the dynamic range in the difference image $I_D = F^M = |I1 - I2|$. More specifically, the minimum and maximum image value is determined and the weights are clipped to this range such that for instance the minimum and maximum values are mapped to the boundary of the unit interval.

In more detail, and in embodiments, values in the difference image $I_D$ that are large in absolute value with respect to the level of residual noise left after de-noising are located at volume regions where the original image I1 suffer from patient motion. With this reasoning we construct the weights image $I_w$ assigned with real values between 0 and 1. By convention, the following encoding may be adopted: weights close to "1" correspond to absolute values in $I_D$ that are similar to or smaller than the level of the residual noise, i.e. to image locations where no patient motion is observed, whilst weights closer to "0" indicate more and more motion. Values in between 0,1 indicate motion presence in between the two extremes. Other encodings, where the role of "0","1" is reversed, or others still, are also envisaged.

The calculation of the weights can be done separately pixel by pixel as in (3) or (4) below. Optionally the obtained weights are convolved with a 2D or 3D smoothing filter for better results.

Suitable monotone weight functions $I_w$ are for instance a positive section of a sinusoidal curve such as the cosine function cos( ) on $[0, \pi]$ or a letter-S-shaped function, with zero tangent slopes at the boundary of the unit interval, such as the softmax-function or related functions. The following two examples illustrate the weight function $I_w$ and are envisaged in some embodiments:

$$I_w(i) = \cos\left(\frac{\pi}{2} \cdot \frac{\tilde{D}(i) - D_1}{\tilde{D}(i) - D_2}\right)^2, \text{ where } \tilde{D} = \min(\max(\text{abs}(I_D(i)), D_1), D_2) \quad (3)$$

$$I_w(i) = \frac{e^x}{e^x + 1}, \text{ where } x = \frac{\delta - \text{abs}(I_D(i))}{\Delta} \quad (4)$$

In (3) and (4), $I_D(i)$ stands for the difference between the two de-noised images at a given image location (eg. pixel of voxel) i. The parameters $D_1$ and $D_2$ in (3) correspond to the image dynamic range. The two parameters are for example two positive HU levels that may be set typically to 15 and 50 respectively. Typical values to use for an example range in (4) for $\delta$ and $\Delta$ are 30 HU and 5 HU, respectively. The range parameters $D_1, D_2/\delta, \Delta$ are not limiting and serve as an illustration only.

The functions at (1), (2) are exemplary embodiments of the weight function $I_w$, and other monotone functions with zero tangent slope at least one of the boundaries of the unit interval are also envisaged. Such functions with zero slope(s) allow for a more realistic modeling with smoothing behaviors at the boundaries. But other function $I_w$ still are also not excluded herein, such as a linear function for example.

The proposed motion artifact reduction method does not require any form of cardiac or respiratory gating.

The proposed motion artifact reduction method allows reducing computational overhead otherwise required in motion compensated reconstructions.

The motion or weight map $I_w$ as computed at step S340 to control the combination operation S360 may be performed one-off, and may be reused for other follow-up reconstructions. Weight reuse may be of particular benefit when computing various types of spectral imagery.

The components of the motion reduction system SYS may be implemented as one or more software modules, run on one or more general-purpose processing units PU such as a workstation associated with the imager XI, or on a server computer associated with a group of imagers.

Alternatively, some or all components of the motion reduction system SYS may be arranged in hardware such as a suitably programmed microcontroller or microprocessor, such an FPGA (field-programmable-gate-array) or as a hard-wired IC chip, an application specific integrated circuitry (ASIC), integrated into the imaging system XI. In a further embodiment still, the motion reduction system SYS may be implemented in both, partly in software and partly in hardware.

The different components of the motion reduction system SYS may be implemented on a single data processing unit PU. Alternatively, some or more components are implemented on different processing units PU, possibly remotely arranged in a distributed architecture and connectable in a suitable communication network such as in a cloud setting or client-server setup, etc.

One or more features described herein can be configured or implemented as or with circuitry encoded within a computer-readable medium, and/or combinations thereof. Circuitry may include discrete and/or integrated circuitry, a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for motion artifact reduction in X-ray imaging, comprising:
   one or more input interfaces for receiving a first input image of an object reconstructed from a first set of projection data, and a second input image of the object reconstructed from a second set of projection data, the second set being smaller than the first set;
   a motion analyzer configured to establish an estimate for motion corruption based on the two input images; and
   a selective combiner configured to compute an image value for an enhanced image based on the motion estimate and image information in the first input image and/or the second input image, wherein the selective combiner is configured to combine the image information from either one or both of the input images such that a relative contribution of image information from the two input images varies with the motion estimate.

2. The system of claim 1, wherein the selective combiner is configured to combine the image information from either one or both of the input images so that a contribution of image information from the first or second input image varies with the motion estimate, at the expense of a contribution of image information from the second and first input image, respectively.

3. The system of claim 2, wherein the contribution of information from the second image is greater, the higher the level of motion corruption indicative by the motion estimate, and wherein the contribution of information from the first image is greater, the lower the level of motion corruption indicative by the motion estimate.

4. The system of claim 1, wherein the relative contribution is determined by a hard or a soft threshold scheme.

5. The system of claim 1, comprising a denoiser applied to initial input images to obtain the two input images as received at the one or more input interfaces.

6. The system of claim 1, wherein the projection data is acquired by computed tomography imaging apparatus.

7. A method for motion artifact reduction in X-ray imaging, comprising:
- receiving a first input image of an object reconstructed from a first set of projection data, and a second input image of the object reconstructed from a second set of projection data, the second set being smaller than the first set;
- establishing an estimate for motion corruption based on the two input images; and
- computing, by a selective combiner, an image value for an enhanced image based on the motion estimate and image information in the first input image and/or the second input image, wherein the selective combiner is configured to combine the image information from either one or both of the input images such that a relative contribution of image information from the two input images varies with the motion estimate.

8. A non-transitory computer-readable medium for storing executable instructions, which cause a method to be performed for motion artifact reduction in X-ray imaging, the method comprising:
- receiving a first input image of an object reconstructed from a first set of projection data, and a second input image of the object reconstructed from a second set of projection data, the second set being smaller than the first set;
- establishing an estimate for motion corruption based on the two input images; and
- computing, by a selective combiner, an image value for an enhanced image based on the motion estimate and image information in the first input image and/or the second input image, wherein the selective combiner is configured to combine the image information from either one or both of the input images such that a relative contribution of image information from the two input images varies with the motion estimate.

\* \* \* \* \*